US00PP32121P2

(12) United States Plant Patent
Stemkens

(10) Patent No.: US PP32,121 P2
(45) Date of Patent: Aug. 25, 2020

(54) ***LEUCANTHEMUM*PLANT NAMED 'Q3597-2'**

(50) Latin Name: ***Leucanthemum* x *superbum***
Varietal Denomination: Q3597-2

(71) Applicant: Henricus Godefridus Wilhelmus Stemkens, Andijk (NL)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/501,817

(22) Filed: Jun. 11, 2019

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./263.1, 285
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Leucanthemum* plant named 'Q3597-2', characterized by its compact, upright and mounded plant habit; freely branching habit; strong and upright flowering stems; no requirement for vernalization treatments to induce flowering; long flowering period; medium-sized single inflorescences with light yellow to creamy white-colored ray florets and bright yellow-colored disc florets; and good garden performance.

2 Drawing Sheets

Botanical designation: *Leucanthemum* x *superbum*.
Cultivar denomination: 'Q3597-2'.

BACKGROUND OF THE INVENTION

The present invention relates to a new and distinct cultivar of *Leucanthemum* plant, botanically known as *Leucanthemum* x *superbum* and hereinafter referred to by the name 'Q3597-2'.

The new *Leucanthemum* plant is a product of a planned breeding program conducted by the Inventor in Enkhuizen, The Netherlands. The objective of the breeding program is to create new uniform *Leucanthemum* plants with numerous attractive inflorescences and no requirement for vernalization to induce flowering.

The new *Leucanthemum* plant originated from an open-pollination during the summer of 2012 of a proprietary selection of *Leucanthemum* x *superbum* identified as code designation P4509-2, not patented, as the female, or seed, parent with an unknown selection of *Leucanthemum* x *superbum* as the male, or pollen, parent. The new *Leucanthemum* plant was discovered and selected by the Inventor as a single flowering plant from within the progeny of the stated open-pollination in a controlled environment in Enkhuizen, The Netherlands on Jul. 18, 2013.

Asexual reproduction of the new *Leucanthemum* plant by vegetative terminal cuttings in Enkhuizen, The Netherlands, since Aug. 23, 2013 has shown that the unique features of this new *Leucanthemum* plant are stable and reproduced true to type in successive generations.

SUMMARY OF THE INVENTION

Plants of the new *Leucanthemum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Q3597-2'. These characteristics in combination distinguish 'Q3597-2' as a new and distinct *Leucanthemum* plant:

1. Compact, upright and mounded plant habit.
2. Freely branching habit.
3. Strong and upright flowering stems.
4. No requirement for vernalization to induce flowering.
5. Long flowering period.
6. Medium-sized single inflorescences with light yellow to creamy white-colored ray florets and bright yellow-colored disc florets.
7. Good garden performance.

Plants of the new *Leucanthemum* differ primarily from plants of the female parent selection in the following characteristics:

1. Plants of the new *Leucanthemum* are more compact than plants of the female parent selection.
2. Ray florets of plants of the new *Leucanthemum* are light yellow to creamy white in color whereas ray florets of plants of the female parent selection are white in color.

Plants of the new *Leucanthemum* can be compared to plants of *Leucanthemum* x *superbum* 'Banana Cream', disclosed in U.S. Plant Pat. No. 23,181. In side-by-side comparisons, plants of the new *Leucanthemum* differ from plants of 'Banana Cream' in the following characteristics:

1. Plants of the new *Leucanthemum* are more compact than plants of 'Banana Cream'.
2. Plants of the new *Leucanthemum* do not require a vernalization treatment to induce flowering whereas plants of 'Banana Cream' require a vernalization treatment to induce flowering.

3. Plants of the new *Leucanthemum* have smaller inflorescences than plants of 'Banana Cream'.

Plants of the new *Leucanthemum* can also be compared to plants of *Leucanthemum maximum* 'LEUZ0001', disclosed in U.S. Plant Pat. No. 23,426. In side-by-side comparisons, plants of the new *Leucanthemum* differ from plants of 'LEUZ0001' in the following characteristics:

1. Plants of the new *Leucanthemum* have single type inflorescences whereas plants of 'LEUZ0001' have semi-double type inflorescences.
2. Ray florets of plants of the new *Leucanthemum* are light yellow to creamy white in color whereas ray florets of plants of 'LEUZ0001' are white in color.

BRIEF DESCRIPTION OF THE PHOTOGRAPHS

The accompanying colored photographs illustrate the overall appearance of the new *Leucanthemum* plant showing the colors as true as it is reasonably possible to obtain in colored reproductions of this type. Colors in the photographs may differ slightly from the color values cited in the detailed botanical description which accurately describe the colors of the new *Leucanthemum* plant.

The photograph on the first sheet is a side perspective view of a typical flowering plant of 'Q3597-2' grown in a container.

The photograph on the second sheet is a close-up view of a typical flowering plant of 'Q3597-2'.

DETAILED BOTANICAL DESCRIPTION

The aforementioned photographs and following observations and measurements describe plants grown in 20-cm containers during the early spring in an outdoor nursery in Lancaster, Pa. and under cultural practices typical of commercial *Leucanthemum* production. During the production of the plants, day temperatures averaged 20° C. and night temperatures averaged 18° C. Plants were 14 weeks old when the photographs and description were taken. In the following description, color references are made to The Royal Horticultural Society Colour Chart, 2015 Edition, except where general terms of ordinary dictionary significance are used.

Botanical classification: *Leucanthemum* x *superbum* 'Q3597-2'.

Parentage:

*Female, or seed, parent*.—Proprietary selection of *Leucanthemum* x *superbum* identified as code designation P4509-2, not patented.

*Male, or pollen, parent*.—Unknown selection of *Leucanthemum* x *superbum*, not patented.

Propagation:

*Type*.—Terminal vegetative cuttings.

*Time to initiate roots, summer*.—About ten to eleven days at temperatures about 18° C.

*Time to initiate roots, winter*.—About eleven to twelve days at temperatures about 18° C.

*Time to produce a rooted young plant, summer*.—About three weeks at temperatures about 16° C.

*Time to produce a rooted young plant, winter*.—About 3.5 weeks at temperatures about 16° C.

*Root description*.—Medium in thickness, fleshy; typically close to 2C in color, actual color of the roots is dependent on substrate composition, water quality, fertilizer type and formulation, substrate temperature and physiological age of roots.

*Rooting habit*.—Moderately freely branching, medium density.

Plant description:

*Plant and growth habit*.—Herbaceous perennial; compact, upright and mounded plant habit; moderately vigorous growth habit; moderate growth rate; freely branching habit with about 20 primary branches (peduncles) developing per plant.

*Plant height*.—About 24 cm.

*Plant width*.—About 31.5 cm.

*Branch (peduncle) description*.—Length: About 22.5 cm. Diameter: At the base, about 7 mm. Internode length: About 1.2 cm. Strength: Strong, flexible. Aspect: Mostly erect to about 10° from vertical. Texture and luster: Moderately pubescent; ridged; semi-glossy. Color: Close to 144A.

*Leaf description*.—Arrangement: Alternate; simple; sessile. Length: About 9.75 cm. Width: About 1.5 cm. Shape: Linear. Apex: Emarginate. Base: Decurrent. Margin: Serrate. Texture and luster, upper surface: Smooth, glabrous; slightly glossy. Texture and luster, lower surface: Sparsely pubescent along the veins and margins; slightly glossy. Venation pattern: Prominent midvein, parallel. Color: Developing leaves, upper surface: Close to 146A. Developing leaves, lower surface: Close to 146B. Fully developed leaves, upper surface: Close to 147A; venation, close to 146A. Fully developed leaves, lower surface: Close to 146A to 146B; venation, close to 146A to 146B.

Inflorescence description:

*Appearance*.—Single inflorescence form with linear-shaped ray florets and tubular disc florets; inflorescences held upright on strong peduncles, inflorescences face mostly upright; ray and disc florets develop acropetally on a capitulum; vernalization treatments are not required to induce flowering.

*Fragrance*.—None detected.

*Flowering response*.—Plants begin flowering about twelve weeks after planting; plants flower naturally during the early spring in Pennsylvania; long flowering period, plants will continue to flower for about five months.

*Inflorescence longevity*.—Depending on temperature, inflorescences maintain good substance for about one to two weeks on the plant; inflorescences persistent.

*Quantity of inflorescences*.—Freely flowering habit, about 20 inflorescences develop per plant at one time.

*Inflorescence size*.—Diameter: About 6.5 cm. Depth (height): About 2.5 cm. Disc diameter: About 1.6 cm.

*Receptacles*.—Height: About 5 mm. Diameter: About 1.2 cm. Color: Close to 144B to 144C.

*Inflorescence buds*.—Height: About 8 mm. Diameter: About 1.1 cm. Shape: Flattened sphere. Color: Close. to 144A.

*Ray florets*.—Quantity per inflorescence: About 42 arranged in about two to three whorls. Length: About 3.2 cm. Width: About 6 mm. Shape: Linear. Apex: Emarginate. Base: Fused into a short tube. Margin: Entire; not undulate. Aspect: Initially upright to about 45° from vertical, with development, curling downward. Texture and luster, upper and lower surfaces: Smooth, glabrous; satiny; slightly glossy.

Color: When opening, upper surface: Close to 4A to 4B. When opening, lower surface: Close to 4B to 4C. Fully opened, upper surface: Close to 157A; venation, close to 157A; color does not change with development. Fully opened, lower surface: Close to N155B to NN155C; venation, close to NN155B to NN155C; color does not change with development.

*Disc florets*.—Quantity per inflorescence: About 210 massed at the center of the receptacle arranged in numerous whorls. Length: About 8 mm. Diameter: About 2 mm. Shape: Fused tubular. Apex: Acute, five-pointed. Texture and luster, inner and outer surfaces: Smooth, glabrous; somewhat glossy. Color, when opening: Apex: Close to 9A. Mid-section and base: Close to 154B to 154C; at the base, close to NN155B to NN155C. Color, fully opened: Apex: Close to 12A. Mid-section and base: Close to 154B to 154C; at the base, close to NN155B to NN155C.

*Involucral bracts*.—Quantity per inflorescence: About 45 arranged in about three or four whorls. Length: About 7.5 mm. Width: About 3.5 mm. Shape: Lanceolate. Apex: Acute. Base: Fused. Margin: Entire, membraneous. Texture and luster, upper surface: Smooth, glabrous; somewhat glossy. Texture and luster, lower surface: Smooth, glabrous; moderately glossy. Color, upper surface: Close to 144A. Color, lower surface: Close to 144B.

*Reproductive organs*.—Androecium: Present on disc florets only. Quantity per floret: Five per disc floret. Filament length: About 6 mm. Filament color: Close to 154D. Anther shape: Roughly rectangular. Anther length: Less than 1 mm. Anther color: Close to 10A. Pollen amount: None observed. Gynoecium: Present on ray and disc florets. Quantity per floret: One. Pistil length: About 7 mm. Stigma diameter: Less than 1 mm. Stigma shape: Bi-parted. Stigma color: Close to 9A. Style length: About 6 mm. Style color: Close to 154D. Ovary color: Close to 154C.

*Seeds and fruits*.—To date, seed and fruit development have not been observed on plants of the new *Leucanthemum*.

Pathogen & pest resistance: To date, plants of the new *Leucanthemum* have not been observed to be resistant to pathogens and pests common to *Leucanthemum* plants.

Garden performance: Plants of the new *Leucanthemum* have been observed to have good garden performance and to tolerate full sunlight, wind and rain, to tolerate temperatures ranging from −22° C. to 38° C.

It is claimed:

1. A new and distinct *Leucanthemum* plant named 'Q3597-2' as illustrated and described.

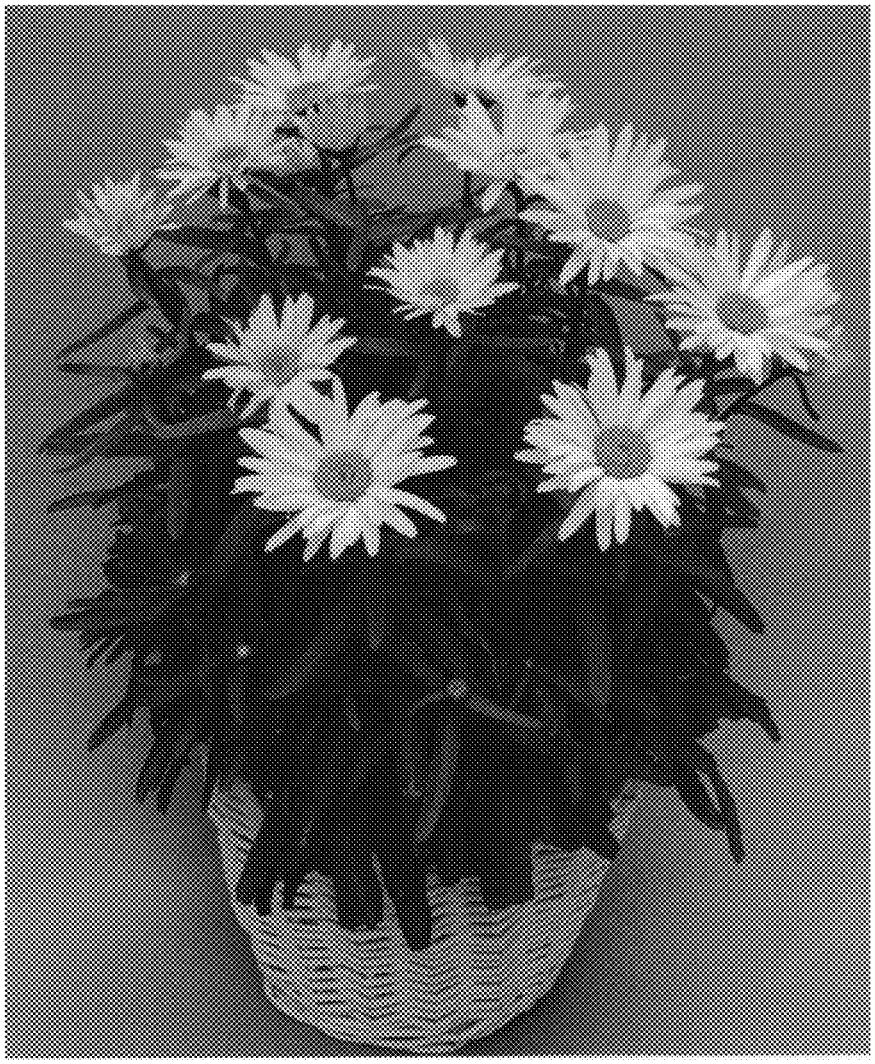

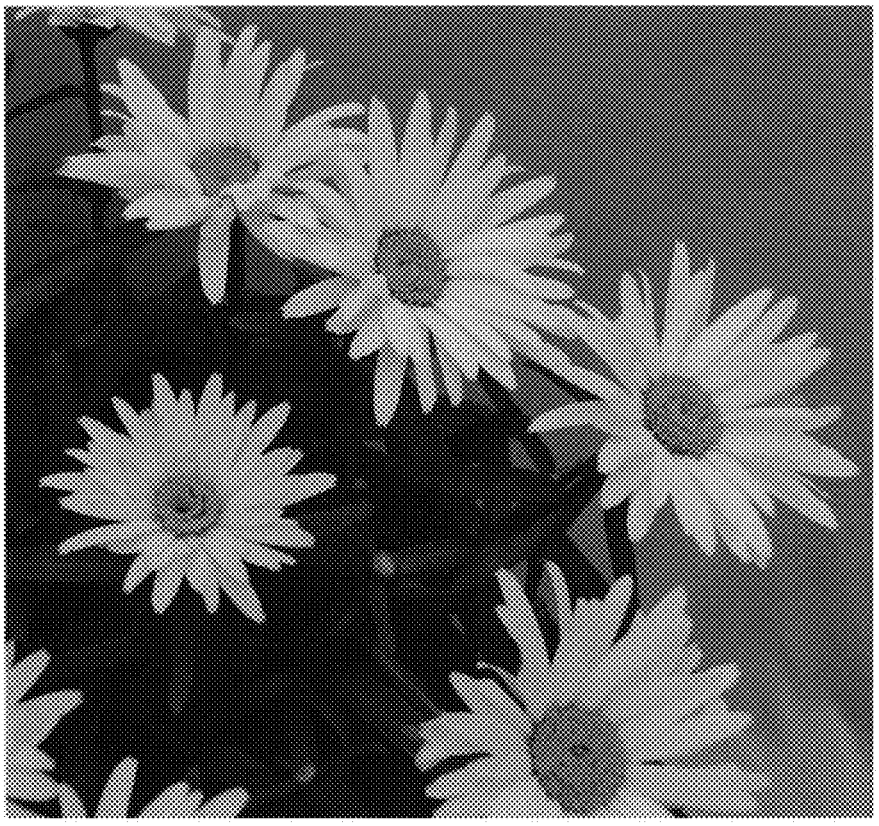

* * * * *